United States Patent [19]

Demay et al.

[11] Patent Number: 4,599,323

[45] Date of Patent: Jul. 8, 1986

[54] CATALYTIC SYSTEM FOR THE HYDROFORMYLATION OF OLEFINS PROCESS OF HYDROFORMYLATION

[75] Inventors: Claude Demay, Voisins le Bretonneux; Claude Bourgeois, Montigny le Bretonneux, both of France

[73] Assignee: CDF Chimie Specialites, Paris, France

[21] Appl. No.: 694,556

[22] PCT Filed: Apr. 24, 1984

[86] PCT No.: PCT/FR84/00115

§ 371 Date: Dec. 24, 1984

§ 102(e) Date: Dec. 24, 1984

[87] PCT Pub. No.: WO84/04299

PCT Pub. Date: Nov. 8, 1984

[30] Foreign Application Priority Data

Apr. 22, 1983 [FR] France ................................ 83 06649

[51] Int. Cl.$^4$ ............................................. B01J 31/20

[52] U.S. Cl. ...................................... 502/161; 568/454
[58] Field of Search ............................................ 502/161

[56] References Cited

U.S. PATENT DOCUMENTS

| | | | |
|---|---|---|---|
| 3,661,949 | 5/1972 | Fenton | 502/161 X |
| 3,876,672 | 4/1975 | Mrowca | 568/454 |
| 4,306,086 | 12/1981 | Demay | 502/161 X |
| 4,522,932 | 6/1985 | Mitchell | 502/161 X |

FOREIGN PATENT DOCUMENTS 2395246 1/1979 France .

*Primary Examiner*—Patrick P. Garvin
*Attorney, Agent, or Firm*—Millen & White

[57] ABSTRACT

A hydroformylation catalyst system consisting essentially of a complex combination (1) of rhodium, carbon monoxide and triarylphosphine or triarylphosphite ligand, a compound (2) of cobalt and a triarylphosphine or triarylphosphite compound (3), wherein said system contains a source of at least one conjugated diene (4).

7 Claims, No Drawings

CATALYTIC SYSTEM FOR THE HYDROFORMYLATION OF OLEFINS PROCESS OF HYDROFORMYLATION

The present invention relates to a catalytic system for the hydroformylation of olefins, still called the OXO reaction. It also relates to a catalytic system for this hydroformylation process. Processes for the hydroformylation of an olefin to produce aldehydes or alcohols having one carbon atom more than the starting olefin consists of reacting this olefin with a synthesis gas in the presence of a catalyst complex containing a transition metal. Among such metals, there are particularly employed metals of Group VIII of the periodic classification, that is to say iron, cobalt, nickel, ruthenium, rhodium, palladium, osmium, iridium and platinum.

These metals can be employed in the form of metal carbonyls, but it is known that these complex combinations contain, in addition to the metal and carbon oxide, at least one biphilic ligand such as a phosphine, leading to more linear products and permitting the process to be operated under low synthesis gas pressures. Such combinations are, for example, described in French Pat. No. 1,300,404 or in U.S. Pat. No. 3,239,566.

These metals can be utilized alone, but certain patents describe the utilization of combinations thereof. Thus, in French Pat. No. 2,395,246, metal couples associated with phosphines are employed for the hydroformylation of internal olefins. In French Pat. No. 2,459,683, the rhodium-cobalt couple associated with triphenylphosphine yields advantages which relate to the aging of the catalyst for the hydroformylation of propylene.

According to the invention, the catalyst system comprising:
(1) a rhodium compound;
(2) a cobalt compound;
(3) a triorganophosphorous compound;
(4) a conjugated diene,
yields unexpectedly, a much higher activity than those activities which are generally obtainable with known catalysts.

This is all the more surprising since conjugated dienes are known to be inhibitors, even catalyst poisons in the oxosynthesis: J. Falbe, "New Synthesis with Carbon Monoxide", Springer-Verlag, New York, 1980. Similar comments can be drawn from French Pat. No. 2,361,324.

By conjugated dienes are meant molecules having the molecular structure

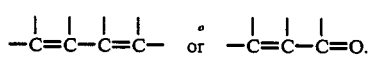

These structures can be incorporated in aliphatic, alicyclic, heterocyclic or aromatic molecules. Also included in this invention are compounds of which the molecules are generated in situ during the course of a hydroformylation reaction to yield a structure such as those which are described above; for example, it is the case with diketones or quinones that tautomeric or chemical equilibrium generate conjugated dienes. Employed either alone or in a mixture, the diene can be introduced in the form of a complex combination with one or two metals, coming within a scope of the invention, as for example in the form of cobalt dicarboxyl cyclopentadienyl or cobalt acetyl acetonate. In this case, the ratio of cobalt to diene is fixed; to obtain a different ratio, it will be necessary eventually to add supplemental diene which, moreover, can be different than the combined diene.

For purposes of illustration, the following are some non-limitative examples of conjugated dienes or metal-diene combination:

Ethyl-2 hexen-2 al

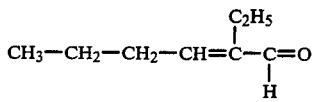

Ethyl-2 methyl-4 penten-2 al

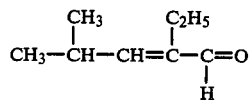

Acetylacetone

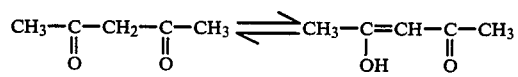

Diphenyl-1,4 butadiene-1,3

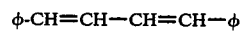

Mesityl oxide

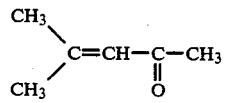

Isophorone

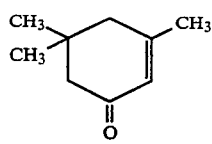

Triphenyl-1,2,5 phosphole

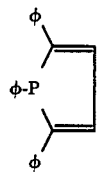

Cyclopentadienyl cobalt dicarbonyl $C_5H_5Co(CO)_2$

Butadiene-1,3

$CH_2=CH-CH=CH_2$

Cyclopentadiene

Hydroquinone

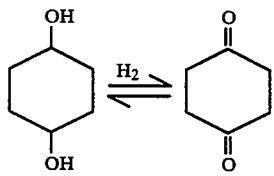

1.5-dimethyl-2-cyano-pyrrole

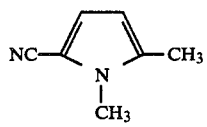

The rhodium compound is a complex of rhodium, carbon oxide and a triorganophosphorous ligand. The employment of such combination, taken alone, as an OXO catalyst is known. In general, more satisfactory results are obtained when the triphosphorous ligand is selected from arylphosphines or arylphosphites. An example of such a combination, when the ligand is triphenylphosphine, is rhodium (I) hydrogenocarbonyl tris (triphenylphosphine) of the formula H Rh CO (P$\phi_3$)$_3$.

Cobalt can be efficiently introduced into the reaction medium in a great variety of forms. For the most part, compounds containing cobalt can be utilized. For example, cobalt can be introduced in the form a carbonyl such as $Co_2(CO)_8$ or $H Co(CO)_4$; one can likewise employ cobalt in the form of a mineral salt or an organic salt such as cobalt acetate, cobalt acetylacetonate, cobalt benzoate, or cobalt naphthenate. Obviously, the cobalt compound employed should not carry any group capable of being a poison for the OXO reaction itself; it is known that chloride or sulphide irons are catalyst poisons for the OXO synthesis. Such compounds are cited in particular in the book by J. Falbe "Carbon Monoxide in Organic Synthesis" Springer-Verlag, N.Y. 1970 or in French Pat. No. 2,377,991. Generally, when the cobalt is introduced as a carbonyl, catalytic activity is obtained nearly instantaneously. In contrast, when cobalt is introduced in the form of an organic or mineral salt, an induction period of some tens of minutes is observed, during the course of which there are probably formed catalytic species in situ. It is believed that the cobalt enters into combination with the diverse components of the reaction medium. This comment is only a hypothesis of an explanation of the observed phenomenon and should not be considered as constituting any limitation as to the scope of the present invention inasmuch as other explanations are certainly possible.

The triorganophosphorous compound is selected from among arylphosphines or arylphosphites; it is not obligatary that the organophosphorous ligand be introduced in the same manner with the rhodium but when such is the case, an excess of this ligand can be considered to be present in the reaction medium.

The rhodium concentrations can be comprised between $10^{-4}$ and $10^{-1}$ mole per liter of reaction solution, but satisfactory results are also obtained when the concentrations are between $10^{-3}$ and $10^{-2}$ per liter.

The quantities of cobalt can be introduced in concentrations of between $10^{-4}$ and 1 mole per liter of reaction solution. When the cobalt concentrations employed are high, there can be observed, in certain cases, precipitates due to the solubility limit of organo-metallic complexes in the reaction medium. This solubility evidently depends on the reaction solvent. If it is desirable to avoid such precipitates, it would be necessary to determine the cobalt concentrations which are permitted so as not to exceed the solubility limit. In practice, the reaction is generally conducted with concentrations between $2\times10^{-4}$ and 0.2 moles/liter.

The concentration of diene is between $5\times10^{-3}$ and 350 g/liter of reaction solution. Good results are generally obtained with concentrations between $5\times10^{-2}$ and 200 g/liter.

It has also been observed however that for certain dienes, the catalyst system yields satisfactory results even when the concentrations in diene are very low, whereas higher concentrations can lead to a retardation of the reaction even up to a complete termination of same. This phenomenon has for example, been noted in the case of acrolein which leads to satisfactory results when in concentrations equal to 0.4 g/liter, but where the reaction is terminated when the concentrations are equal to 35 g/liter. In contrast, for example, in the case of ethyl-2 hexene-2 al, the concentrations can be increased without any problem up to more than 200 g/l. One can speculate that certain properties of the diene, for example steric hindrance or electronic factors influence the stability of the complexes involved in the catalytic process, and consequently the concentrations of diene for which the catalytic system is particularly efficacious should be variable from one diene to the other. The concentration ranges previously indicated for the dienes are given as indications only and are generally suitable for the majority of dienes. The technologist in this field can, after routine classical experiments, select the most appropriate values for the concentration for any given diene, that is to say values which do not lead to an inhibition of the reaction.

Organophosphorous ligands such as arylphosphines or arylphosphites can be utilized in molar ratios of phosphor/rhodium higher than 10.

The hydroformylation of the olefins with the present catalyst system is conducted generally at a temperature between abut 60° C. and about 150° C., with temperatures between 80° C. and 125° C. being more often employed. The total pressure of hydrogen and carbon monoxide being rather low is between about 1 and 40 bars, and the molar ratio $H_2/CO$ is about between 1/1 and 20/1.

The process can be conducted by passing to the reaction zone a feedstream composed of a mixture of hydrogen and carbon monoxide, the olefinic charge to be hydroformylated, and a new or recycled catalyst dissolved in a solvent or in the heavy reaction products.

The reaction product can be recovered from the reaction medium by distillation of a liquid stream withdrawn continuously from the reaction, the heavy products containing the catalyst being eventually recycled as already discussed above. Reaction products can also be recovered by extracting them directly from the reaction medium by entrainment in a current of gas withdrawn from the reaction zone, which can be, for example, excess synthesis gas. This process presents the advantage of permtting the catalyst system to remain in place, but it can be applied conveniently only for the hydroformylation of light olefins such as propylene, butenes, or pentenes.

Generally, the complexes are introduced at the beginning of the reaction in order to obtain a substantial improvement in activity in relationship to known catalysts. When the OXO reaction is conducted on a basis of rhodium and organophosphorous complexes as described previously without the introduction, starting from the beginning of cobalt and diene, a much weaker catalyst activity is noted and this activity decreases in time. If the cobalt and diene are then added, a substantial degree of the activity is recovered. Thus, according to the latter procedure, the addition of cobalt and diene during the course of the reaction can also be considered as a regeneration of the already known catalyst system of rhodium and a triorganophosphorous ligand.

The following examples, without limitative character, illustrate the invention.

EXAMPLE 1

In a general manner, the following experiments 1 to 19 are conducted in a 200 ml stainless steel autoclave equipped with an agitator, temperature measuring means and gas feed piping. There are introduced 20 ml of n-butanal, 43 mg of hydridocarbonyl triphenylphosphine rhodium (H Rh CO (P$\phi_3$)$_3$) and 1.33 g of triphenylphosphine P$\phi_3$. There is next added the cobalt and diene in the proportions designated in Table 1. After the autoclave is closed and subjected to agitation, the autoclave is heated in order to attain a temperature of 95° C.; the relative pressure is then 1.8 bar. In the autoclave the following partial pressures are established:

| Propylene | 2 bars |
| Carbon Monoxide | 1.7 bar |
| Hydrogen | 5.5 bars |

The relative total pressure, which then reaches 10 bars, is maintained at this value by the continuous addition of a gaseous mixture CO/H$_2$/propylene in a ratio of 1/1/1. The yields are expressed in grams of aldehyde per hour per gram of rhodium. The yields calculated in Table 1 are values which exclude the eventual induction periods associated with the likely formation in situ of the active catalytic species.

Tests 1 to 4 are given for purposes of comparison. Tests 1 and 2 illustrate the harmful effective of dienes on conventional catalysts. They show that the addition of a diene to a catalyst system constituted of a rhodium complex and a phosphine, or constituted of a cobalt complex results in a considerable lowering and even the complete destruction of the activity of the catalyst.

TABLE 1

| Test | Cobalt, expressed as the atomic ratio Co/Rh | Diene expressed in g/liter | Yield expressed in g/h × gRh |
|---|---|---|---|
| 1 | 275 ppm Rh without Co | Ethyl-2 hexene-2 al 164 | 86 |
| 2 | 700 ppm of Co in the form of Co$_2$(CO)$_8$ without Rh | Ethyl-2 hexene-2 al 164 | 0 |
| 3 | 275 ppm Rh without Co | O | 531 |
| 4 | Co$_2$(CO)$_8$ 5/1 | O | 616 |
| 5 | Co$_2$(CO)$_8$ 5/1 | Ethyl-2 hexene-2 al 164 | 725 |
| 6 | Co$_2$(CO)$_8$ 1/1 | Ethyl-2 hexene-2 al 164 | 775 |
| 7 | Co$_2$(CO)$_8$ 5/1 | Acrolein 0.4 | 631 |
| 8 | Co$_2$(CO)$_8$ 5/1 | Mesityl oxide 168 | 797 |
| 9 | Co$_2$(CO)$_8$ 5/1 | Butadiene-1,3 7.8 | 651 |
| 10 | Co$_2$(CO)$_8$ 5/1 | Diphenyl-1,4 butadiene- 1.5 1,3 | 711 |
| 11 | Co$_2$(CO)$_8$ 5/1 | Dimethyl-1,5 2 pyrrole- 9 carbonitrile | 636 |
| 12 | Co$_2$(CO)$_8$ 5/1 | Hydroquinone 1.3 | 674 |
| 13 | Co$_2$(CO)$_8$ 5/1 | Cyclopentadiene 44.4 | 623 |
| 14 | (C$_5$H$_5$) Co (CO)$_2$ 5/1 | / | 723 |
| 15 | (Ac. Ac.)$_2$ Co(II) 5/1 | Ethyl-2 hexene-2 al 33 | 835 |
| 16 | Co$_2$(CO)$_8$ 5/1 | Iriphenyl-1,2,5, 2.2 phosphole | 652 |
| 17 | Co$_2$(CO)$_8$ 5/1 | Pentaphenyl-1,2,3, 3.3 4,5 phosphole | 780 |
| 18 | Co$_2$(CO)$_8$ 5/1 | Benzoquinone 0.7 | 841 |
| 19 | Co$_2$(CO)$_8$ 5/1 | Furfural 98.6 | 720 |

EXAMPLE 2

The next tests 20–31 are conducted in the same type of apparatus permitting tests of long duration and in accordance with the same operating conditions as the tests of Example 1. The phosphorous/rhodium ratio is close to 100. In this series of tests, the cobalt-diene system is added after a certain aging time of the catalyst (HRhCO(P$\phi_3$)$_3$).

TABLE 2

| Test | Time of Aging in Hours | [Rh] in ppm | Cobalt expressed as the atomic ration Co/Rh | Diene expressed in g/liter | Yield expressed in g/h × gRh |
|---|---|---|---|---|---|
| 20 | 0 | 440 | O | O | 358 |
| 21 | 394 | 565 | O | O | 241 |
| 22 | 394 | 452 | Co$_2$(CO)$_8$ 5/1 | Ethyl-2 hexene-2 al 146 | 419 |
| 23 | 394 | 452 | Co$_2$(CO)$_8$ 5/1 | Acetylactone 167 | 681 |
| 24 | 654 | 520 | O | O | 200 |
| 25 | 654 | 420 | Co$_2$(CO)$_8$ 5/1 | Ethyl-2 hexene-2 al 146 | 427 |
| 26 | 654 | 420 | Co$_2$(CO)$_8$ 5/1 | Ethyl-2 methyl-4 146 pentene-2 al | 369 |
| 27 | 654 | 420 | Co$_2$(CO)$_8$ 5/1 | Mesityl oxide 146 | 336 |
| 28 | 789 | 500 | O | O | 174 |
| 29 | 789 | 400 | Co$_2$(CO)$_8$ 5/1 | Ethyl-2 hexene-2 al 146 | 318 |
| 30 | 789 | 400 | Co$_2$(CO)$_8$ 1/1 | Ethyl-2 hexene-2 al 146 | 292 |
| 31 | 789 | 500 | Co$_2$(CO)$_8$ 5/1 | Butadiene-1,3 16.8 | 269 |

EXAMPLE 3

The next experiments 32–34 relate to the hydroformylation of hexene-1, and are conducted in a stainless steel 200 ml autoclave equipped with an agitator, temperature measuring means and piping to be used for the feeding of gas. There is introduced 10 ml of toluene, 10 ml of hexene-1, 40 mg of hydridocarbonyltristriphenylphosphine rhodium (H Rh CO ((P$\phi_3$)$_3$) and 1,2 g of triphenylphosphine (P$\phi_3$). There is finally added cobalt and diene in the proportions indicated in Table 3. After closure and starting agitation, the autoclave is heated to attain a temperature of 80° C.; the relative pressure is 1 bar. There is established in the autoclave the following partial pressures

| Carbon Monoxide | 1 bar |
|---|---|
| Hydrogen | 5 bars |

The relative total pressure which then attains 7 bars, is maintained at this value by the continuous addition of a gaseous mixture of $H_2$/CO in a ratio of 1/1. After 25 minutes of reaction time, both the agitation and the feeding of the gas is terminated, and the autoclave is then cooled and degassed. The reaction mixture is analyzed by gas chromatography and the yield is expressed in grams of aldehyde formed per hour and per gram of rhodium (g/hxgRh).

Example 32 is given for purposes of comparison.

TABLE 3

| Test | Cobalt expressed as the atomic ration Co/Rh | Diene expressed in g/liter | Yield expressed in g/h × gRh |
|---|---|---|---|
| 32 | 275 ppm Rh without Co | 0 | 1007 |
| 33 | $C_5H_5$ Co(CO)$_2$ 10/1 | / | 1791 |
| 34 | Co$_2$(CO)$_8$ 5/1 | pentaphenyl-1,2,3,4,5 phosphole 3 | 2456 |

We claim:

1. A catalyst system consisting essentially of a complex combination (1) of rhodium, carbon monoxide and a triarylphosphine or triarylphosphite ligand, a compound (2) of cobalt and a triarylphosphine or triarylphosphite compound (3) wherein said system contains a source of at least one conjugated diene (4).

2. A catalyst system according to claim 1, wherein the conjugated diene is an aliphatic alicyclic, heterocyclic or aromatic molecule containing the sequence

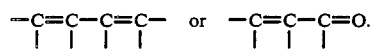

3. A catalyst system according to one of claims 1 and 2 wherein the conjugated diene exists in complex combination with one of the two metals.

4. A catalyst system according to claim 1, wherein a compound generating in situ a conjugated diene (4) is added to the combination of (1), (2) and (3) during the course of the reaction.

5. A catalyst system according to claim 2, wherein a compound generating in situ a conjugated diene (4) is added to the combination of (1), (2) and (3) during the course of the reaction.

6. A catalyst system according to claim 3, wherein a compound generating in situ a conjugated diene (4) is added to the combination of (1), (2) and (3) during the course of the reaction.

7. In a catalyst system for the hydroformylation of olefins, comprising (1) rhodium, carbon monoxide and a triorganophosphorous ligand, (2) a cobalt compound, and (3) a triorganophosphorous compound,
the improvement wherein a source of (4) at least one conjugated diene is added to said system.

* * * * *